(12) United States Patent
Wu et al.

(10) Patent No.: US 10,238,701 B2
(45) Date of Patent: Mar. 26, 2019

(54) COMPOSITION OF WOOD EAR, SHIITAKE, HAWTHORN FRUIT, ROSELLE, CELERY AND FRUIT OF CHINESE PLUM FOR TREATMENT AND/OR PREVENTION OF HYPERLIPIDEMIA, ATHEROGENESIS AND OBESITY

(71) Applicant: TAIPEI MEDICAL UNIVERSITY, Taipei (TW)

(72) Inventors: Chieh-Hsi Wu, Taipei (TW); Chun-Hsu Pan, Taipei (TW); Chi-Han Wu, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 15/294,139

(22) Filed: Oct. 14, 2016

(65) Prior Publication Data
US 2018/0104291 A1    Apr. 19, 2018

(51) Int. Cl.
| | | |
|---|---|---|
| A61K 36/07 | (2006.01) | |
| A61K 36/734 | (2006.01) | |
| A61K 36/185 | (2006.01) | |
| A61K 36/23 | (2006.01) | |
| A61K 36/736 | (2006.01) | |
| A23L 33/105 | (2016.01) | |

(52) U.S. Cl.
CPC ............ *A61K 36/07* (2013.01); *A23L 33/105* (2016.08); *A61K 36/185* (2013.01); *A61K 36/23* (2013.01); *A61K 36/734* (2013.01); *A61K 36/736* (2013.01); *A61K 2236/30* (2013.01); *A61K 2236/37* (2013.01)

(58) Field of Classification Search
None
See application file for complete search history.

(56) References Cited

U.S. PATENT DOCUMENTS

2013/0164391 A1* 6/2013 Kim .................... A61K 8/97
424/735
2017/0042778 A1* 2/2017 Carle ................... A61K 8/347

OTHER PUBLICATIONS

Aziz Z., et al. Effects of *Hibiscus sabdariffa* L. on serum lipids: a systematic review and meta-analysis, JJournal of Ethnopharmacology, 2013,150, 442-450.
Bisen P.S. et al., Lentinus edodes: a macrofungus with pharmacological activities, Current Medicinal Chemistry, 2010, 17, 2419-2430.
Fukushima, M. et al., Cholesterol-lowering effects of maitake (*Grifola frondosa*) fiber, shiitake (*Lentinus edodes*) fiber, and enokitake (*Flammulina velutipes*) fiber in rats, Exp Biol Med (Maywood), 2001, 226, 758-765.
Tsi, D., et al. Effects of aqueous celery (*Apium graveolens*) extract on lipid parameters of rats fed a high fat diet, Planta Med, 1995, 61, 18-21.
Zeng, F. et al., Chemical properties of a polysaccharide purified from solid-state fermentation of Auricularia auricular and its biological activity as a hypolipidemic agent, Journal of Food Science, 78, 2013, H1470-1475.
Zhang, J. et al., Effects of an aqueous extract of *Crataegus pinnatifida* Bge. var. major N.E.Br. fruit on experimental atherosclerosis in rats, Journal of Ethnopharmacology148(2013)563-569.
Chi-Han Wu et al., Antiobesity and antihyperlipidaemic effects of Yan-Sheng-Yin in animals and humans, Journal of Functional Foods 24 (2016)173-182.
Office action from the Taiwan patent office for application 105133347 dated Jul. 19, 2017.
Reza et al., Hypolipidemic and hepatic steatosis preventing activities of the wood ear medicial mushroom *Auricularia auricula-judae* (higher basidiomycetes) ethanol extract in vivo and in vitro, Int J Med Mushrooms, 2015, 17 (8):723-34. (Abstract).
Peter C.K. Cheung Ph.D., The hypocholestrolemic effect of two edible mushrooms: *Auricularia auricula* (tree-ear) and *Tremella fuciformis* (white jelly-leaf) in hypercholesterolimic rats, Nutrition Research, Oct. 1996, pp. 1721-1725, vol. 16, Issue 10, Elsevier Inc. (Abstract).
Bozena et al., Edible mushrooms in prophylaxis and treatment of human diseases, MIR N-ro 4 (101), Dec. 2013, pp. 170-183, vol. 25-a. (Abstract and conclusion).
Lee et al., Anti-obesity effects of Lentinus edodes on obese mice induced by high fat diet, J Korean Soc Food Sci Nutr, 2014, 43(2, pp. 194-199. (Abstract).
Li et al., Effects of pectin pentaoligosaccharide from hawthorn (*Crataegus pinnatifida* Bunge. var. Major) on the activity and mRNA levels of enzymes involved in fatty acid oxidation in the liver of mice fed a high-fat diet, J Agric Food Chem., Aug. 2013, 61(31):7599-605. (Abstract).
Sharma et al., Hypocholesterolemic and antioxidant potentials of some plants and herbs: a review, Research and Reviews: Journal of Zoological Sciences, Oct.-Dec. 2013, pp. 26-37, vol. 1 Issue 2, (p. 35).
Chang et al., Hibiscus sabdariffa extract inhibits obesity and fat accumulation, and improves liver steatosis in humans, Food Funct., Apr. 2014, 5(4):734-9. (Abstract).
Hibiscus sabdariffa, Oct. 22, 2011, 10 pages. The introduction on papers relevant to roselle.
Chung Shan Med J, 2004, p. 153. (Abstract).
Research & Development. Journal of Food and Biotechnology, 2008, pp. 62-69, No. 14.
Apium graveolens, May 6, 2012, 6 pages.The introduction on papers relevant to Apium graveolens.
Patra et al., Review of medicinal plants for anti-obesity activity, Translational Biomedicine, 2015, pp. 1-10, vol. 6 No. 3:21, USA. (Table 1).

(Continued)

*Primary Examiner* — Ralph J Gitomer
(74) *Attorney, Agent, or Firm* — WPAT, P.C., Intellectual Property Attorneys; Anthony King

(57) ABSTRACT

The invention provides a water extract of Yan-Sheng-Yin (YSY), a Chinese natural dietary supplement for treatment and/or prevention of hyperlipidemia, atherogenesis and obesity, comprised entirely of natural foods and a preparation comprising the same.

9 Claims, 11 Drawing Sheets

(56) References Cited

OTHER PUBLICATIONS

Determinatin of chlorogenic acid in hawthorn by HPLC, Journal of Pharmaceutical Practice, 2012, 30(6):457-458. (Abstract).
English translation of examiners opinion regarding the patentability of the subject application.

* cited by examiner

COMPOSITION OF WOOD EAR, SHIITAKE, HAWTHORN FRUIT, ROSELLE, CELERY AND FRUIT OF CHINESE PLUM FOR TREATMENT AND/OR PREVENTION OF HYPERLIPIDEMIA, ATHEROGENESIS AND OBESITY

FIELD OF THE INVENTION

The invention provides a water extract of Yan-Sheng-Yin (YSY), a Chinese natural dietary supplement for health promotion, comprised entirely of natural foods and a preparation comprising the same. The invention also provides a method for treatment and/or prevention of hyperlipidemia, atherogenesis and obesity.

BACKGROUND OF THE INVENTION

Patients suffering from both obesity and hyperlipidemia are exposed to high risk of cardiovascular disease, as well as reducing body's white adipose tissue (WAT) could minimize risk of chronic cardiovascular disorders. Many weight-loss drugs have been reported to elevate the risk for cardiovascular diseases. Besides, statins, a class of cholesterol lowering drugs, have also been noticed to have mild to severe side effects. Therefore, researchers seek an alternative therapy to apply on anti-obesity and anti-hyperlipidemia.

During the progression of obesity, WAT mass expansion was thought to depend on both the adipocyte hyperplasia and hypertrophy. Thereby, adipocyte differentiation (from the preadipocytes into the adipocytes) was characterized as a major cellular process that positively associated with obesity. Two critical transcription factors, peroxisome proliferator-activated receptors (PPARs) and CCAAT/enhancer-binging proteins (C/EBPs), played the pivotal role to regulate the transcription activities of the genes associated with adipocyte differentiation. Increased C/EBP-β might produce PPAR-γ ligand to trigger PPAR-γ-mediated signaling pathways resulting in adipocyte differentiation and adipogenesis. Besides, 5'AMP-activated protein kinase (AMPK) can increase fatty acid oxidation by inhibit acetyl-CoA carboxylase (ACC) as well as reduce cholesterol synthesis by suppressing HMG-CoA reductase (HMGCR), respectively. Previous reports revealed that plasma level of adiponectin in the obese patients or mice is lower than lean subjects. Adiponectin, one of adipokines secreted by adipocytes, was able to promote adipocyte differentiation and to modulate energy metabolism by stimulate AMPK activation.

Some of plant ingredients within YSY prescription have been reported to exhibit the potential activities on anti-hyperlipidemic or anti-atherogenic effects (Aziz, Z, Wong, S. Y., & Chong, N. J. (2013). *Effects of Hibiscus sabdariffa L. on serum lipids: a systematic review and meta-analysis. J Ethnopharmacol*, 150, 442-450; Bisen, P. S., Baghel, R. K., Sanodiya, B. S., Thakur, G. S., & Prasad, G. B. (2010). *Lentinus edodes: a macrofungus with pharmacological activities. Curr Med Chem*, 17, 2419-2430; Fukushima, M., Ohashi, T., Fujiwara, Y., Sonoyama, K., & Nakano, M. (2001). *Cholesterol-lowering effects of maitake (Grifola frondosa) fiber, shiitake (Lentinus edodes) fiber, and enokitake (Flammulina velutipes) fiber in rats. Exp Biol Med (Maywood)*, 226, 758-765; Tsi, D., Das, N. P., & Tan, B. K. (1995). *Effects of aqueous celery (Apium graveolens) extract on lipid parameters of rats fed a high fat diet. Planta Med*, 61, 18-21; Zeng, F., Zhao, C., Pang, J., Lin, Z, Huang, Y., & Liu, B. (2013). *Chemical properties of a polysaccharide purified from solid-state fermentation of Auricularia auricular and its biological activity as a hypolipidemic agent. J Food Sci*, 78, H1470-1475; Zhang, J., Liang, R., Wang, L, Yan, R., Hou, R., Gao, S., & Yang, B. (2013). *Effects of an aqueous extract of Crataegus pinnatifida Bge. var. major N.E.Br. fruit on experimental atherosclerosis in rats. J Ethnopharmacol*, 148, 563-569). Although single plant ingredient can provide inhibitory effects on hyperlipidemia, the multi-ingredient products might exhibit excellent synergistic activities.

SUMMARY OF THE INVENTION

In the invention, the inhibitory effects and mechanisms of water extract of Yan-Sheng-Yin (YSY), a Chinese natural dietary supplement for health promotion on hyperlipidemia, atherogenesis and obesity are investigated. The invention indicates that the water extract of YSY activates 5'AMP-activated protein kinase (AMPK) to promote lipid metabolism. Besides, the invention also demonstrates that the water extract of YSY suppressed peroxisome proliferator-activated receptor-gamma (PPAR-γ) and CCAAT/enhancer-binging proteins (C/EBPs) to inhibit adipocyte differentiation as well as increases adiponectin secretion to promote lipid metabolism. The invention suggests that the water extract of YSY can be used as an adjuvant intervention for the treatment and prevention of hyperlipidemia, atherogenesis and obesity.

The invention provides a water extract of a composition comprising wood ear (*Auricularia auricular*), shiitake (*Lentinus edodes*), hawthorn fruit (*Crataegus pinnatifida*), roselle (*Hibiscus sabdariffa*), celery (*Apium graveolens*) and fruit of Chinese plum (*Prunus mume*), wherein the water extract is obtained by mixing wood ear, shiitake, hawthorn fruit, roselle, celery and fruit of Chinese plum to form a composition, soaking the composition in water for at least 16 hours at a temperature of about 50° C. to about 80° C. and cooking the resulting composition to boil to obtain the water extract of the composition.

The invention also provides a water extract of a composition comprising wood ear (*Auricularia auricular*), shiitake (*Lentinus edodes*), hawthorn fruit (*Crataegus pinnatifida*), roselle (*Hibiscus sabdariffa*), celery (*Apium graveolens*) and fruit of Chinese plum (*Prunus mume*), wherein the composition having retention time at about 3.2 to about 4.5 minutes (preferably about 3.978 minutes) and about 5.4 to about 6.2 minutes (about 5.943 minutes), respectively, as measured by HPLC.

The invention also provides a preparation comprising the water extract of the invention.

The invention further provides a method for treating and/or preventing a hyperlipidemia, atherogenesis and/or obesity, comprising administering an effective amount of the water extract of the invention to a subject.

DETAILED DESCRIPTION OF THE INVENTION

Figure 1:
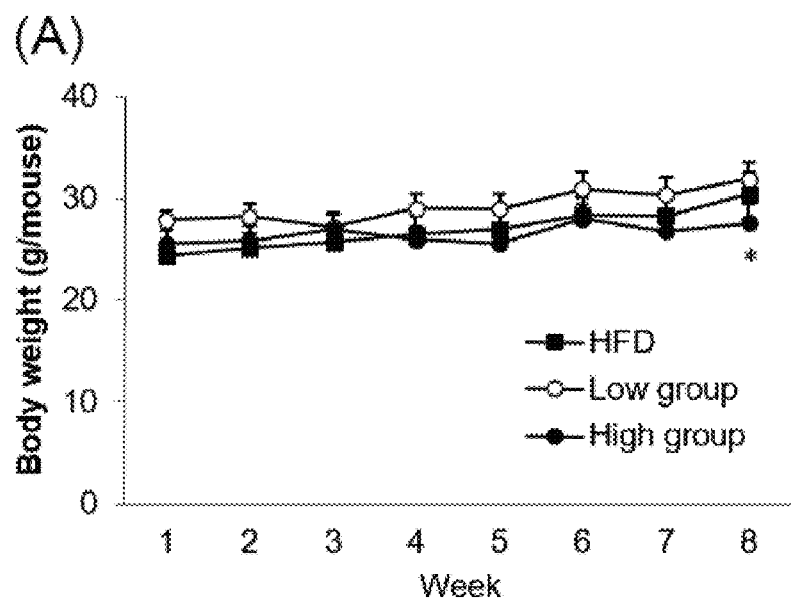
FIGS. 1 (A) to (C) show anti-obesity and anti-adipogenic effects of YSY in the HFD-fed ApoE-KO mice. The body weight (A) and food intake (C) were recorded every week during the experiment period. Visceral adipose tissues were photographed and weighed to examine the lipid pad ratio (B). * p<0.05 compared to the group treated with HFD alone.
Figure 1:
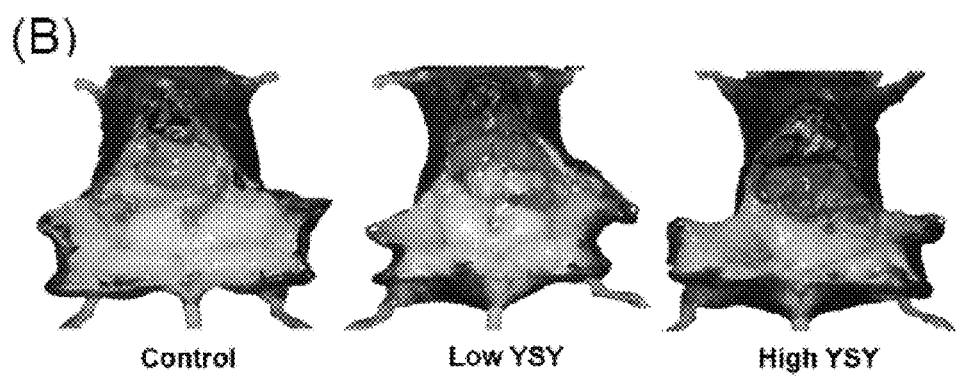
Figure 1:
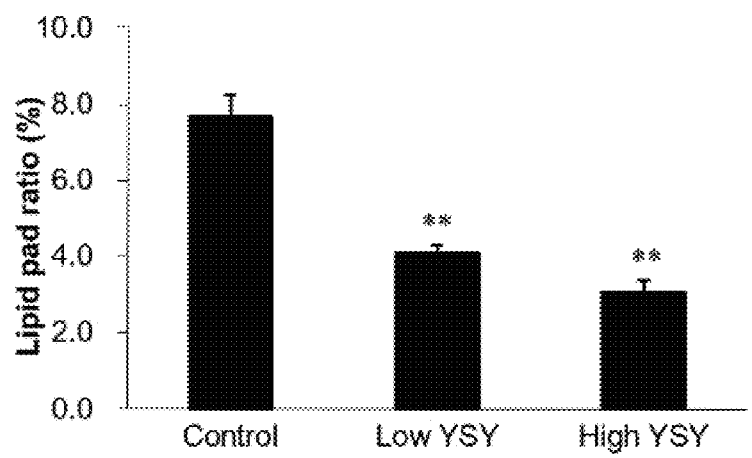
Figure 1:
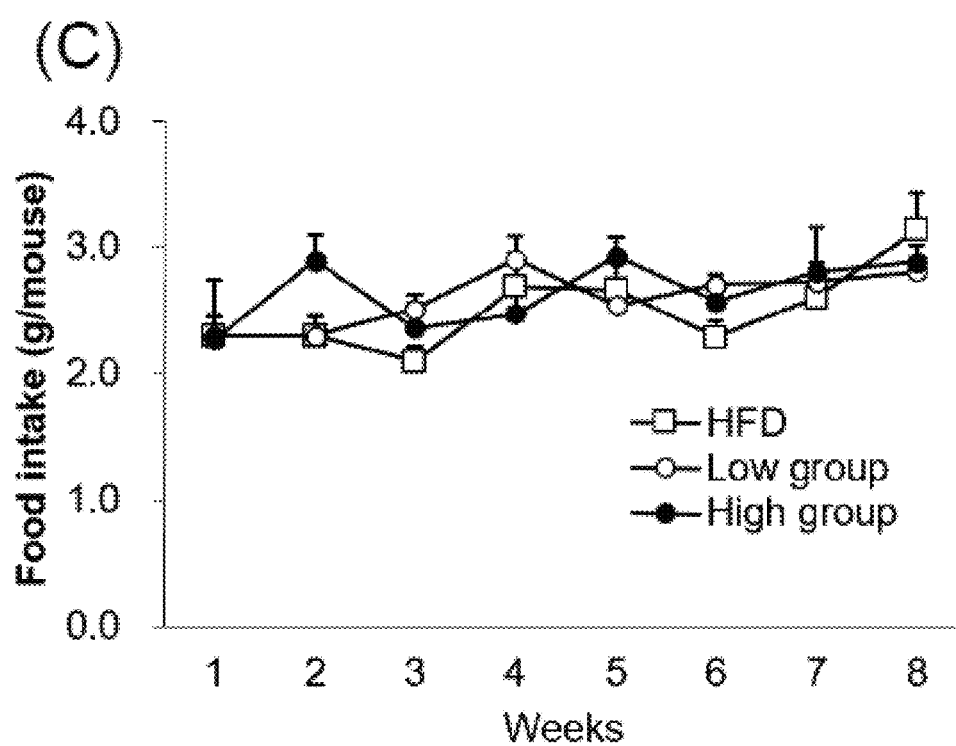

The invention surprisingly found that the water extract of YSY can reduce body weight, hyperlipidemia, fatty liver, and atherogenesis.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The terms "a" and "an" refer to one or to more than one (i.e., to at least one) of the grammatical object of the article.

As used herein, the term "or" in the claims refers to "and/or" unless explicitly indicated to refer to alternatives only or unless the alternatives are mutually exclusive.

The term "promote," "promotion," and "promoting" refer to an increase in an activity, response, condition, disease, or other biological parameter.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the composition of the invention to perform their intended function.

The term "treat" or "treatment" is meant to indicate a method of reducing the effects of a disease or condition. Treatment can also refer to a method of reducing the underlying cause of the disease or condition itself. The treatment can be any reduction from native levels and can be but is not limited to the complete ablation of the disease, condition, or the symptoms of the disease or condition.

The term "prevent," "prevention" or "preventing" means inhibition or averting of symptoms associated with osteoporosis.

The term "effective amount" means an amount of the composition of the invention effective to treat and/or prevent the disease, condition, or the symptoms of the disease or condition.

In one aspect, the invention provides a water extract of a composition comprising wood ear (*Auricularia auricular*), shiitake (*Lentinus edodes*), hawthorn fruit (*Crataegus pinnatifida*), roselle (*Hibiscus sabdariffa*), celery (*Apium graveolens*) and fruit of Chinese plum (*Prunus mume*), wherein the water extract is obtained by mixing wood ear, shiitake, hawthorn fruit, roselle, celery and fruit of Chinese plum to form a composition, soaking the composition in water for at least 16 hours at a temperature of about 50° C. to about 80° C. and cooking the resulting composition to boil to obtain the water extract of the composition. The resulting extract can be detected by HPLC.

In one embodiment, the soaking time of composition is about 18 hours to about 48 hours, about 18 hours to about 46 hours, about 18 hours to about 44 hours, about 18 hours to about 42 hours, about 18 hours to about 40 hours, about 18 hours to about 38 hours, about 18 hours to about 36 hours, about 18 hours to about 44 hours, about 18 hours to about 42 hours, about 18 hours to about 40 hours, about 18 hours to about 38 hours, about 18 hours to about 36 hours, about 18 hours to about 34 hours, about 18 hours to about 32 hours, about 18 hours to about 30 hours, about 18 hours to about 28 hours, about 18 hours to about 26 hours, about 20 hours to about 48 hours or about 22 hours to about 48 hours. Preferably, the composition is soaked in water for about 24 hours.

In one embodiment, the soaking temperature is about 50° C. to about 75° C., about 50° C. to about 70° C., about 50° C. to about 65° C., about 55° C. to about 75° C. or about 55° C. to about 70° C. Preferably, the soaking temperature is about 60° C.

In one embodiment, wood ear, shiitake, hawthorn fruit, roselle, celery and fruit of Chinese plum in the composition are in a ratio of about 0.5 to about 1.5:about 0.5 to about 1.5:about 1.5 to about 2.5:about 1.5 to about 2.5:about 4.5 to about 5.5:about 0.5 to about 1.5 by dry weigh. Preferably, the ratio is about 1:about 1:about 2:about 2:about 5:about 1 by dry weight.

In another aspect, the invention provides a water extract of a composition comprising wood ear (*Auricularia auricular*), shiitake (*Lentinus edodes*), hawthorn fruit (*Crataegus pinnatifida*), roselle (*Hibiscus sabdariffa*), celery (*Apium graveolens*) and fruit of Chinese plum (*Prunus mume*), wherein the composition comprises compounds having retention time at about 3.2 to about 4.5 minutes (preferably about 3.978 minutes) and about 5.4 to about 6.2 minutes (about 5.943 minutes), respectively, as measured by HPLC.

In one embodiment, the water extract further comprises the compounds having retention times at about 3.2 to about 4.5 minutes (preferably about 3.978 minutes), about 2.7 minutes to 3.2 minutes (preferably 2.995 minutes) and about 5.4 to about 6.2 minutes (about 5.943 minutes), respectively, as measured by HPLC. In one embodiment, the water extract further comprises the compounds having retention times at about 3.2 to about 4.5 minutes (preferably about 3.978 minutes), about 2.7 minutes to 3.2 minutes (preferably 2.995 minutes) and about 5.4 to about 6.2 minutes (preferably about 5.943 minutes), about 2.0 minutes to about 2.5 minutes (preferably about 2.307 minutes), about 9.0 minutes to about 9.4 minutes (preferably about 9.224 minutes) and about 6.8 minutes to 7.1 minutes (preferably about 6.931 minutes), as measured by HPLC. In addition to these peaks, the water extract further comprises the compounds having the retention times at about 0.565 minutes, about 0.751 minutes, about 1.175 minutes, about 7.996 minutes, about 8.361 minutes, about 10.879 minutes, about 11.709 minutes, about 12.303 minutes and about 12.766 minutes as measured by HPLC. In one embodiment, the water extract of the invention has a HPLC profile as shown in FIG. 1.

According to the invention, the water extract of the invention has the HPLC profile as shown in the table below.

| Retention Time | Peak Area | Percentage of weight | Relative Height |
|---|---|---|---|
| 0.565 | 698 | 0.10 | 0.0965 |
| 0.751 | 893 | 0.13 | 0.0470 |
| 1.175 | 70 | 0.01 | 0.0074 |
| 2.307 | 71966 | 10.11 | 23.4407 |
| 2.995 | 53663 | 7.54 | 2.4072 |
| 3.978 | 282367 | 39.67 | 12.5603 |
| 5.943 | 244255 | 34.31 | 6.7734 |
| 6.931 | 18882 | 2.65 | 0.5328 |
| 7.966 | 2449 | 0.34 | 0.1309 |
| 8.361 | 341 | 0.05 | 0.0037 |
| 9.224 | 29862 | 4.19 | 0.9513 |
| 10.879 | 4930 | 0.69 | 0.1585 |
| 11.709 | 1053 | 0.15 | 0.0570 |
| 12.303 | 139 | 0.02 | 0.0185 |
| 12.766 | 304 | 0.04 | 0.0130 |

Any extraction technique known in this art may be employed to prepare the extract according to the invention. The resulting extract can be further fractioned by chromatography. Preferred chromatography is liquid phase chromatography using solvent elution. Preferably, the liquid chromatography is high performance liquid chromatography (HPLC) or reverse-phase HPLC. In one embodiment, the HPLC described herein is conducted by using mobile phase A as ddH$_2$O and mobile phase B as MeOH/formic acid (99.9:0.1 by volume ratio), C18 column and flow rate as 0.5 ml/min and UV detector.

In one aspect, the invention provides a water extract of a composition comprising wood ear (*Auricularia auricular*), shiitake (*Lentinus edodes*), hawthorn fruit (*Crataegus pinnatifida*), roselle (*Hibiscus sabdariffa*), celery (*Apium graveolens*) and fruit of Chinese plum (*Prunus mume*), wherein the composition comprises compounds having retention times at about 4.61 minutes to 4.95 minutes (preferably about 4.67 minutes), about 6.1 minutes to about 6.5 minutes (preferably about 6.29 minutes), about 6.8 minutes to about 7.0 minutes (preferably about 6.91 minutes), about 3.45 minutes to about 3.62 minutes (preferably about 3.53 minutes) and about 2.96 minutes to 3.16 minutes (preferably about 3.06 minutes), respectively as measured by Extracted ion chromatogram (XIC) of multiple reaction monitoring (MRM), wherein the XIC of –MRM is detected at 153.000/109.000 Da of HPLC-MS/MS and protocatechuic acid is used as standard.

In another aspect, In one aspect, the invention provides a water extract of a composition comprising wood ear (*Auricularia auricular*), shiitake (*Lentinus edodes*), hawthorn fruit (*Crataegus pinnatifida*), roselle (*Hibiscus sabdariffa*), celery (*Apium graveolens*) and fruit of Chinese plum (*Prunus mume*), wherein the composition comprises compounds having retention times at about 4.35 minutes to about 4.65 minutes (preferably about 4.52 minutes), about 3.41 minutes to about 3.62 minutes (preferably about 3.55 minutes), about 4.0 minutes to about 4.15 minutes (preferably about 4.09 minutes), about 3.8 minutes to about 4.0 minutes (preferably about 3.95 minutes) and about 5.18 minutes to about 5.4 minutes (preferably about 5.26 minutes), respectively as measured by Extracted ion chromatogram (XIC) of multiple reaction monitoring (MRM), wherein the XIC of –MRM is detected at 153.000/109.000 Da of HPLC-MS/MS and chlorogenic acid is used as standard.

In one aspect, the invention provides a preparation comprising the water extract as defined herein.

In another aspect, the invention provides a method for treating and/or preventing a hyperlipidemia, atherogenesis and/or obesity, comprising administering an effective amount of the water extract of the invention to a subject.

The water extract of the invention can be formulated with a pharmaceutically acceptable carrier, excipient and/or diluent as a pharmaceutically preparation or medicament for administration.

A pharmaceutically acceptable carrier, diluent and/or excipient means that the carrier, diluent and/or excipient must be compatible with the other ingredients of the preparation, does not adversely affect the therapeutic benefit of the water extract of the invention, and is not deleterious to the recipient thereof.

Administration of the water extract or a preparation thereof for practicing the present invention can be by any method that delivers the compounds systemically and/or locally. These methods include oral routes, parenteral routes, intraduodenal routes, etc.

In local applications, the water extract or a preparation thereof is locally applied to the sites in need thereof.

For topical applications, the water extract or a preparation thereof can be formulated in a suitable ointment containing the water extract or a preparation thereof suspended or dissolved in one or more carriers. Carriers for topical administration of the water extract or a preparation thereof of this invention include, but are not limited to, mineral oil, liquid petrolatum, white petrolatum, propylene glycol, polyoxyethylene, polyoxypropylene compound, emulsifying wax, sugars such as lactose and water. Alternatively, the pharmaceutical preparations can be formulated in a suitable lotion or cream containing the water extract or a preparation thereof suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Depending on the particular condition, disorder or disease to be treated, additional therapeutic agents can be administered together with the water extract or a preparation thereof. Those additional agents can be administered sequentially in any order, as part of a multiple dosage regimen, from the water extract-containing composition (consecutive or intermittent administration). Alternatively, those agents can be part of a single dosage form, mixed together with the water extract or a preparation thereof in a single composition (simultaneous or concurrent administration).

For oral administration, a pharmaceutical composition useful in the invention can take the form of solutions, suspensions, tablets, pills, capsules, powders, granules, semisolids, sustained release formulations, elixirs, aerosols, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the water extract or a preparation thereof of this invention can be combined with various sweetening agents, flavoring agents, coloring agents, emulsifying agents and/or suspending agents, as well as such diluents as water, ethanol, propylene glycol, glycerin and various like combinations thereof.

The choice of formulation depends on various factors such as the mode of drug administration (e.g., for oral administration, formulations in the form of tablets, pills or capsules are preferred) and the bioavailability of the drug substance.

The term "parenteral" as used herein refers to modes of administration which include intravenous, intramuscular, intraperitoneal, intrasternal, subcutaneous, intramedullary and intraarticular injection and infusion. A pharmaceutical composition for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Aqueous solutions are especially suitable for intravenous, intramuscular, subcutaneous and intraperitoneal injection purposes. In this connection, the sterile aqueous media employed are all readily obtainable by standard techniques well-known to those skilled in the art. Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical preparations useful in the present invention can also contain adjuvants such as, but not limited to, preservatives, wetting agents, emulsifying agents, and dispersing agents. Prevention of the action of microorganisms can be ensured by the inclusion of various antibacterial and antifungal agents, such as for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents that delay absorption such as aluminum monostearate and gelatin.

Suspensions, in addition to the water extract or a preparation thereof, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For purposes of transdermal (e.g., topical) administration, dilute sterile, aqueous or partially aqueous solutions (usually in about 0.1% to 5% concentration), otherwise similar to the above parenteral solutions, are prepared.

The pharmaceutical preparations useful in the invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

Compositions for rectal or vaginal administration are preferably suppositories which can be prepared by mixing the water extract or a preparation thereof of the invention with suitable non-irritating excipients or carriers such as cocoa butter, polyethylene glycol or a suppository wax which are solid at room temperature but liquid at body temperature and therefore melt in the rectum or vaginal cavity and release the drugs.

Other pharmaceutically acceptable carriers include, but are not limited to, a non-toxic solid, semisolid or liquid filler, diluent, encapsulating material or formulation auxiliary of any type, including but not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solid pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Methods of preparing various pharmaceutical compositions with a certain amount of active ingredient are known, or will be apparent in light of this disclosure, to those skilled in this art. Other suitable pharmaceutical excipients and their formulations are described in Remington's Pharmaceutical Sciences, edited by E. W. Martin, Mack Publishing Company, 19th ed. (1995.

Pharmaceutical compositions useful in the present invention can contain 1%-100% (by weight) of the water extract or a preparation thereof of this invention. In any event, the composition or formulation to be administered will contain a quantity of the water extract or a preparation thereof according to this invention in an amount effective to treat the condition, disorder or disease of the subject being treated.

One of ordinary skill in the art will appreciate that pharmaceutically effective amounts of the water extract or a preparation thereof can be determined empirically and can be employed in pure form or, where such forms exist, in pharmaceutically acceptable salt, ester or prodrug form. The agents can be administered to a patient as pharmaceutical compositions in combination with one or more pharmaceutically acceptable excipients. It will be understood that when administered to, for example, a human patient, the total daily usage of the agents or composition of the present invention will be decided within the scope of sound medical judgment by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. In one embodiment, the effective amount of the water extract of the invention is from about 4 g/day to about 18 g/day. In some embodiments, the effective amount is about 4 g/day to about 16 g/day, about 4 g/day to about 14 g/day, about 4 g/day to about 12 g/day, about 6 g/day to about 18 g/day, about 4 g/day to about 16 g/day, about 6 g/day to about 14 g/day, about 8 g/day to about 18 g/day, about 8 g/day to about 16 g/day, about 8 g/day to about 14 g/day, about 10 g/day to about 18 g/day, about 10 g/day to about 16 g/day or about 8 g/day to about 14 g/day. Preferably, the effective amount is about 12 g/day. Dosage can also be arranged in a patient specific manner to provide a predetermined concentration of the agents in the blood, as determined by techniques accepted and routine in the art.

Alternatively, the water extract or a preparation thereof can be formulated with a food grade carrier excipient, diluent and/or salt as a health food or a dietary supplement. The above-mentioned carrier excipient, diluent and/or salt can be used in the health food or a dietary supplement of the invention. Health food or dietary supplements may exist in various forms, including, but not limited to tablets, capsules, caplets, powders, drinks including shakes, solid food items including snack bars, etc.

It will be readily apparent to one of ordinary skill in the relevant arts that other suitable modifications and adaptations to the methods and applications described herein can be made without departing from the scope of the invention or any embodiment thereof. The following examples are offered to illustrate but not to limit the invention.

EXAMPLES

Materials and Methods
1. Chemicals and Reagents

The antibodies against phospho-ACC (acetyl-CoA carboxylase; #3661), phospho-AMPKα (5'-adenosine monophosphate activated protein kinase-alpha; #2531s), and PPAR-γ (peroxisome proliferator-activated receptor-gamma; #2435) were purchased from the Cell Signaling Technology, Inc. (Danvers, Mass., USA). The antibodies for recognizing β-actin (#ab6276) and C/EBP-β (CCAAT/enhancer binding protein beta; #GTX61124) proteins were acquired from the Abcam (Cambridge, Mass., USA) and the GeneTex, Inc. (USA), respectively. Horseradish peroxide-labelled secondary antibodies against mouse immunoglobulin G (IgG) (#sc2005) and rabbit IgG (#sc2004) were obtained from the Santa Cruz Biotechnology (Santa Cruz, Calif., USA). All other reagents were purchased from Sigma-Aldrich (St Louis, Mo., USA).

2. Preparation of YSY

YSY composed six natural foods including wood ear (*Auricularia auricular*), shiitake (*Lentinus edodes*), hawthorn fruit (*Crataegus pinnatifida*), roselle (*Hibiscus sabdariffa*), celery (*Apium graveolens*) as well as fruit of Chinese plum (*Prunus mume*), and its mixing ratio was 1:1:2:2:5:1 by dry weight. All plants were purchased from the certified farms and its origins were authenticated by the Chinese herbal therapy center, China Medical University Hospital (Taichung, Taiwan). All dry plants were cut into pieces, soaked into water for 24 h at 60° C., and then cooked at 100° C. to concentrate the extracts.

3. Chromatography Profile and Identification of Bioactive Compounds in YSY

Identification of the potential bioactive compounds mentioned previously, such as protocatechuic acid (PCA) and chlorogenic acid (CGA), in YSY were carried out by LC/ESI-MS/MS (Applied Biosystems Sciex, Foster City, Calif., USA) to establish a reference chromatographic profile of YSY extract for quality check of extraction procedure of each batch. LC/ESI-MS/MS analysis was performed using a API 2000-triple quadrupole mass spectrometer (Applied Biosystems/MDS Sciex, Foster City, Calif., USA) equipped with an electrospray ionization source and interfaced with an Agilent 1200 HPLC (Agilent Technologies, Wilmington, Del., USA). YSY (500 µg/mL) were separated with a Syncronis™ C18 column (150×4.6 mm with 5 µm; Thermo, Waltham, Mass., USA). Mobile phase A was ddH$_2$O while mobile phase B was MeOH/formic acid (99.9: 0.1 by volume ratio), and the flow rate was set to 0.5 ml/min. The detector used in HPLC assay is UV detector.

Mass spectrometric analyses were performed using electrospray ionization tandem mass spectrometry in the negative multiple reaction monitoring (MRM) mode. All analytes showed [M-H]$^-$ as the most intensive precursor ion, which could be detected in negative ion mode as [M-H]. Two MRM transitions, one quantifier and one qualifier for each analyte, were detected using 100 ms as dwell time; PCA: 353/191, 353/85; CGA: 153/109, 153/91.

4. Hyperlipidemic Animal Model

All procedures and animal care were approved and carried out in accordance with the institutional animal ethical guidelines of the Laboratory Animal Service Center, China Medical University (Taichung, Taiwan). Male ApoE-KO mice (Four-month-old) were divided into four groups (n=8/group) including Chow diet group (normal diet), HFD (High fat diet; normal diet mixed with 60% fat), HFD+low-dose YSY (0.4 g/kg/day), and HFD+high-dose YSY (2 g/kg/day). Male hamsters (eight-week-old) were divided into eight groups (n=6/group) including HFD, HFD+YSY (1.48 g/kg/day), HFD+*A. auricular* (1.48 g/kg/day), HFD+*L. edodes* (1.48 g/kg/day), HFD+*C. pinnatifida* (1.48 g/kg/day), HFD+*H. sabdariffa* (1.48 g/kg/day), HFD+*A. graveolens* (1.48 g/kg/day), and HFD+*P. mume* (1.48 g/kg/day). The hypolipidemic animals were induced by HFD for 4 weeks and then therapeutic intervention with the extract of YSY or single plant ingredient for further 8 weeks. At the end of the study, animals were anaesthetized by an intramuscular injection of Zoteil 50® (0.1 ml) (Virbac Ltd, Carros, France) and then the biospecimens including blood, liver and visceral adipose tissues were collected to evaluate the histopathological and blood biochemistry examinations.

5. Blood Biochemistry Analysis

After overnight starvation, whole blood was harvested after animal sacrifice by using separator tube, blood samples were allowed to clot for 2 h at room temperature before centrifugation at 1000×g for 20 min at 4° C. Measurement of serum levels of total cholesterol (TC), triglycerides (TG), low-density lipoprotein (LDL), high-density lipoprotein (HDL), glutamate pyruvate transaminase (GPT), and blood urea nitrogen (BUN) were serviced by Zhen-Xing Co., Ltd (Taichung, Taiwan). Besides, serum adiponectin was measured by commercial ELISA kit (#E90605Mu, USCN Life Science Inc., USA) according to the manufacturer's instruction.

6. Cryosection of Liver and Visceral Fat Tissues

The lipid accumulation in liver tissue was carry out according to our previous study (Pan et al., 2013). Liver tissues were perfused with normal saline, fixed in 5% formalin neutralized solution (J. T. Baker, Inc., Philipsburg, N.J., USA) for 24 h, and embedded in Tissue-Tek® OCT compound (#4583, Sakura Finetek Inc., Torrance, Calif., USA). The embedded tissues were cut into 10 μm and stained with Sudan IV (for liver tissues) or Oil Red (for fat tissues) as well as hematoxylin/eosin (Merck, Whitehouse Station, N.J., USA). Photographs were acquired under a 400-fold magnification and quantified on an Alphalmager 2200® documentation system (Alpha InnoTech, San Leandro, Calif., USA).

7. Lipid Pad Analysis

Lipid pad was collected at the end of 8-week study. Perigonadal and flank adipose tissues were dissected and then rinsed with 1× phosphate-buffered saline (PBS). Lipid pad ration was calculated as follow equation (Eq. (1)):

Lipid pad ratio (%)=Perigonadal and flank adipose tissues (g)/Body weight (g)×100     (1)

8. Western Blot

Liver tissues were homogenized with the PRO-PREP® protein extraction solution (500 μl/g), and protein concentration was measured by using the Bio-Rad protein assay (Bio-Rad). Equal amounts (30 μg) of extracted proteins were electrophoresed through 10% SDS-PAGEs and then transferred to polyvinylidene fluoride (PVDF) membranes. The membranes were blocked for 1 h by using 5% non-fat dry milk solved in PBST (1×PBS with 0.1% Tween 20) and then washed with PBST. Membranes were then incubated with specific primary antibodies at the appropriate dilutions (p-ACC, 1:1000; p-AMPK, 1:1000; HMG-CoA, 1:500; PPAR-γ, 1:1000; C/EBP-β, 1:500; β-actin, 1:1000) for 2 h at room temperature. After that, the blots were washed and incubated with HRP-conjugated secondary antibodies at a dilution of 1:2000 for 1 h at room temperature. Luminescence signals were developed with chemiluminescent reagent, acquired by Fujifilm LAS-4000 system (San Leandro, Calif., USA), and quantified using Image J software program from the NIH (USA).

9. Analysis of Aortic Fatty Streak

Aortas were harvested after animal sacrifice and then rinsed gently with normal saline. All tissue samples were incubated in 4% paraformaldehyde for 10 min and then stained with Oil Red solution (5 mg/mL in isopropanol) 15 min at room temperature. The stained aortas were washed with several different concentrations of isopropanol (90%, 70% and 50%) for 1 min, followed by a rinsed with water. Photographs were obtained with a digital camera (#D80; Nikon, Tokyo, Japan).

10. Clinical Study

This human study, an open-label and parallel pilot clinical trial, was approved (#DMR99-IRB-126) by China Medical University Hospital (Taichung, Taiwan) to investigate the lipid-lowering effect of YSY in healthy and hyperlipidemic subjects. Adults of age 22-65 years with hyperlipidemia defined by the Adult Treatment Panel III (ATP III) were considered for enrolment. The participants with pregnant or chronic metabolic diseases were excluded. In addition, all subjects were not using lipid-lowering drugs, such as statins, bile acid sequestrants, fibrates, and nicotinic acid, and the medicines that may alter hepatic functions during the trial period. The eligible participants were divided into three groups (normal, borderline and high groups) according to ATP III guide. The study began with a 4-week baseline period. Blood samples were collected as a blank control before the study. After that, all subjects received 12 g/day of YSY for 2 months. At the end of study, the blood samples were collected at 24 h after YSY administration.

11. Statistical Analysis

Data were expressed as mean±S.D. Analysis of variance was used to assess the statistical significance of the differences followed by Tukey's test for all pair's comparisons. A value of p<0.05 was considered statistically significant. The data were analyzed with the Statistical Package for Social Sciences (SPSS X, Chicago, Ill., USA).

Example 1 YSY Decreases Body Weight, Adipose Tissue Accumulation and Blood Lipids in the HFD-Fed Mice Our experimental data suggested that the body weight and visceral adipose tissue mass were markedly reduced by high-dose treatment of YSY as compared to that of the control group (FIGS. 1A and 1B). For confirming whether the YSY-induced reduction of body weight was due to the change in food intake, food intake was recorded during the experimental period. As shown in FIG. 1C, there was no significant difference among all groups in food intake amount after 8 weeks of study. In the present study, we also explored the hypolipidemic effects of YSY on HFD-fed ApoE-KO mice (Table 1). The experimental results showed that several biochemical parameters (TC, TG and LDL) were significantly decreased after high-dose YSY treatment as compared to the control group (HFD alone). However, the serum level of HDL was not markedly improved by YSY (Table 1). Besides, no significant differences were observed in serum levels of GPT and BUN among all group, implicating no obvious toxicity found after YSY treatment.

TABLE 1

Serum biochemistry profile in the ApoE-KO mice treated with YSY.

| | | HFD | | |
|---|---|---|---|---|
| | Chow diet | Control | Low YSY | High YSY |
| TC (mg/dL) | 438 ± 43 | 494 ± 19[b] | 428 ± 24 | 383 ± 26[a] |
| TG (mg/dL) | 108 ± 15 | 101 ± 4 | 94 ± 4 | 85 ± 4[a] |
| LDL (mg/dL) | 337 ± 20 | 362 ± 26 | 346 ± 17 | 297 ± 27[a] |
| HDL (mg/dL) | 9 ± 1 | 21 ± 2 | 29 ± 2 | 29 ± 2 |
| GPT (U/L) | 50 ± 5 | 84 ± 7 | 88 ± 29 | 66 ± 10 |
| BUN (mg/dL) | 20 ± 1 | 21 ± 2 | 15 ± 1 | 17 ± 1 |

[a]p < 0.05 compared to the control group (treated with HFD alone).
[b]p < 0.05 compared to the chow diet group.

Example 2 YSY Reduces Adipogenesis in the HFD-Fed Mice

Figure 2:
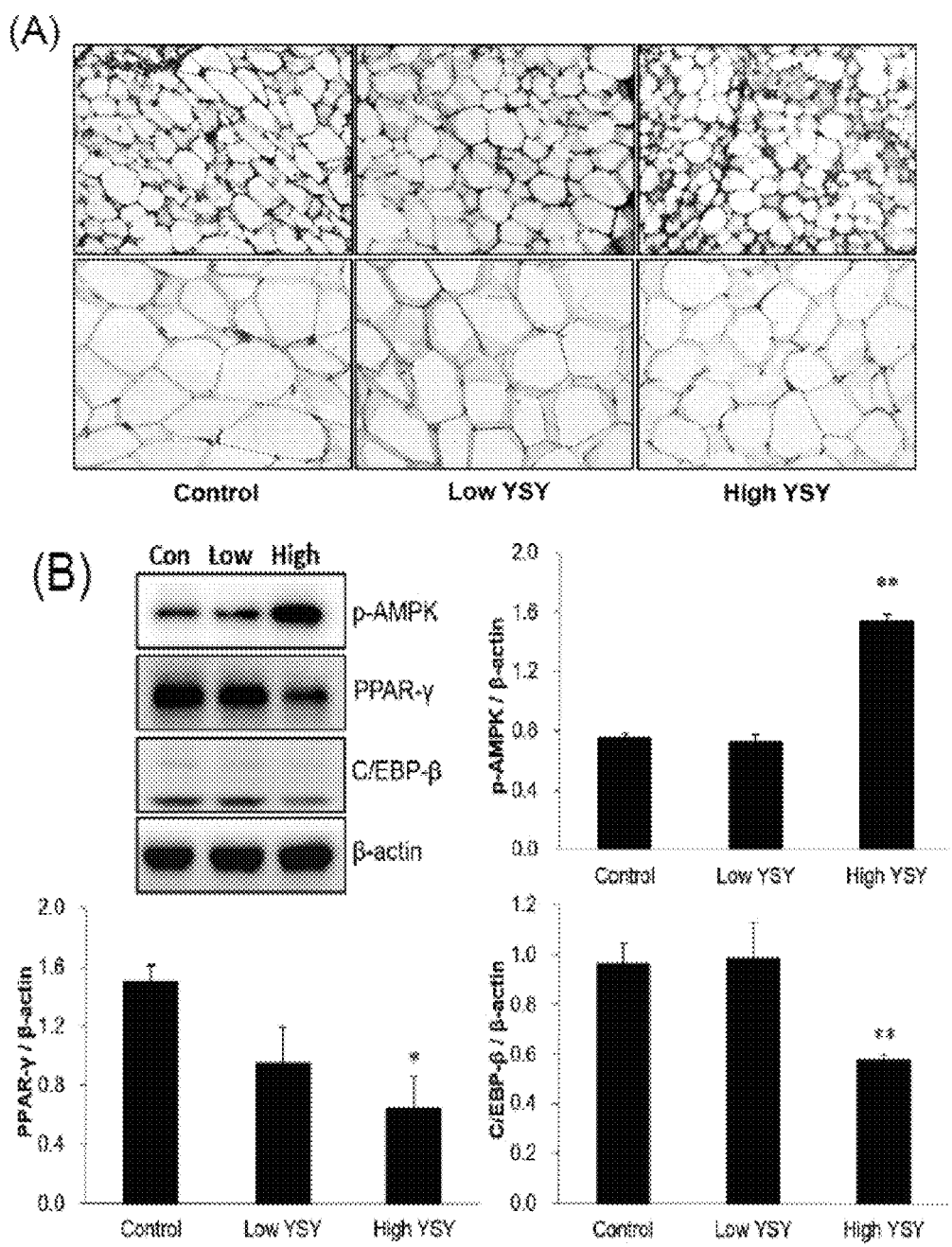
FIGS. 2 (A) to (C) show anti-adipogenic effect and mechanism of YSY in the HFD-fed ApoE-KO mice. Adipocyte size of visceral WAT was discolored with hematoxylin/eosin staining to observe histomorphological changes (A). Adipogenesis-associated molecules (AMPKα, PPAR-γ and C/EBP-β) within WAT were examined by Western blot (B). Serum level of adiponectin was measured by ELISA (C). * p<0.05 compared to the control group (treated with HFD alone).
Figure 2:
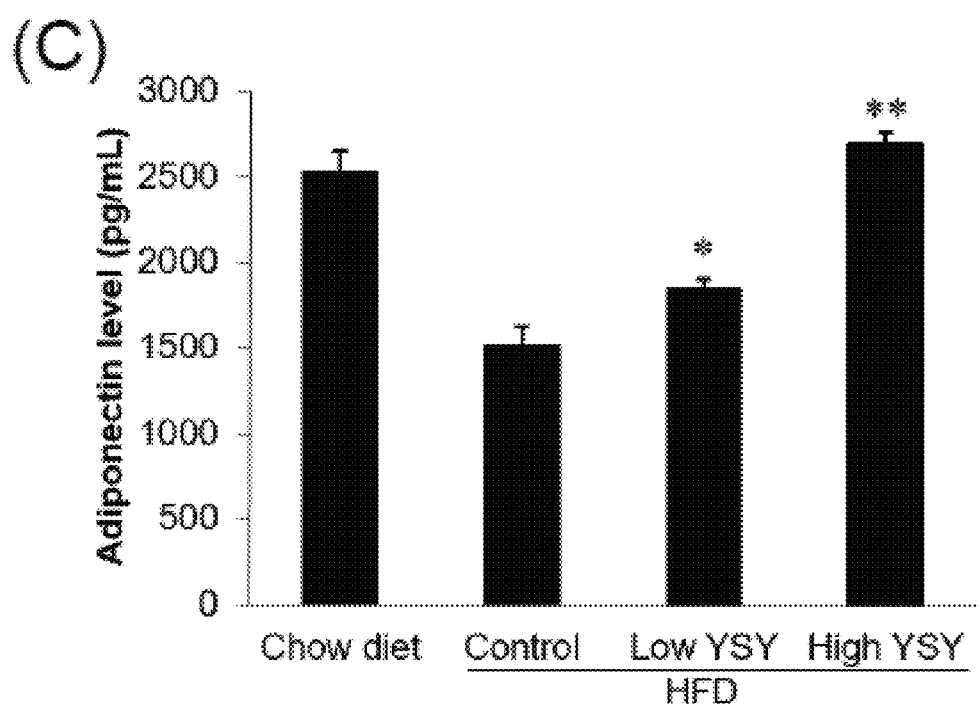

After 8-week of animal study, the visceral adipose tissues were frozen sliced and discolored with HE staining to evaluate the changes of adipocyte size, and the histopathological results suggested that adipocyte size was reduced by high-dose YSY treatment (FIG. 2A), which implicated the YSY may regulate the adipocyte differentiation. Therefore, three pivotal proteins involved in adipocyte differentiation, including AMPK, PPAR-γ and C/EBP-β, were examined to clarify the potential regulations of YSY. Our results showed that YSY increased AMPK phosphorylation and decreased PPAR-γ and C/EBP-β expressions in the group treated with high-dose YSY (FIG. 2B). Because YSY reduced WAT size and inhibited adipogenesis, we further measured the circulating level of adiponectin in the HFD-fed ApoE-KO mice. YSY was found to dose-dependently increase serum level of adiponectin (FIG. 2C).

Figure 3:
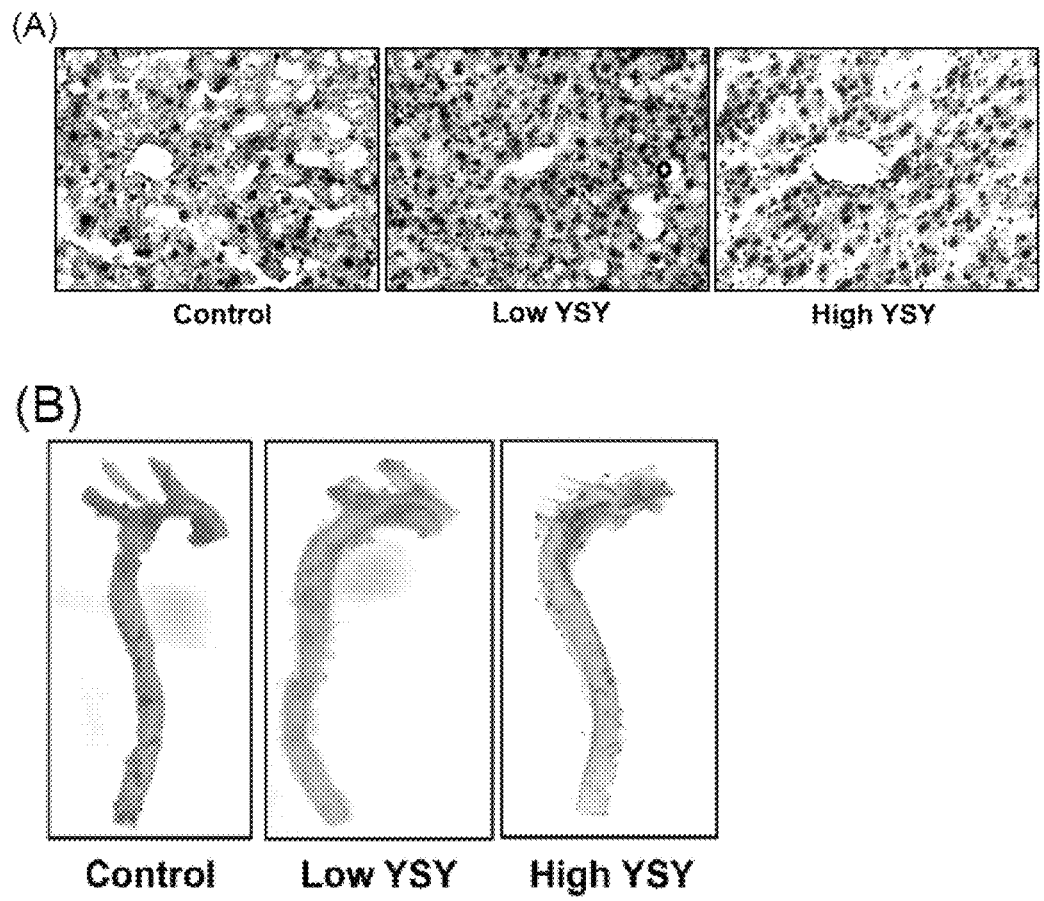
FIGS. 3 (A) to (C) show YSY ameliorated hepatic steatosis and atherosclerosis in the HFD-fed ApoE-KO mice. Hepatic steatosis (A) and aortic fatty streak (B) were visualized by Sudan IV and Oil Red staining, respectively. The lipid metabolism-associated molecules (ACC, AMPK and HMGCR) within liver tissues were determined by immunoblotting (C). * p<0.05 compared to the control group (treated with HFD alone).
Figure 3:
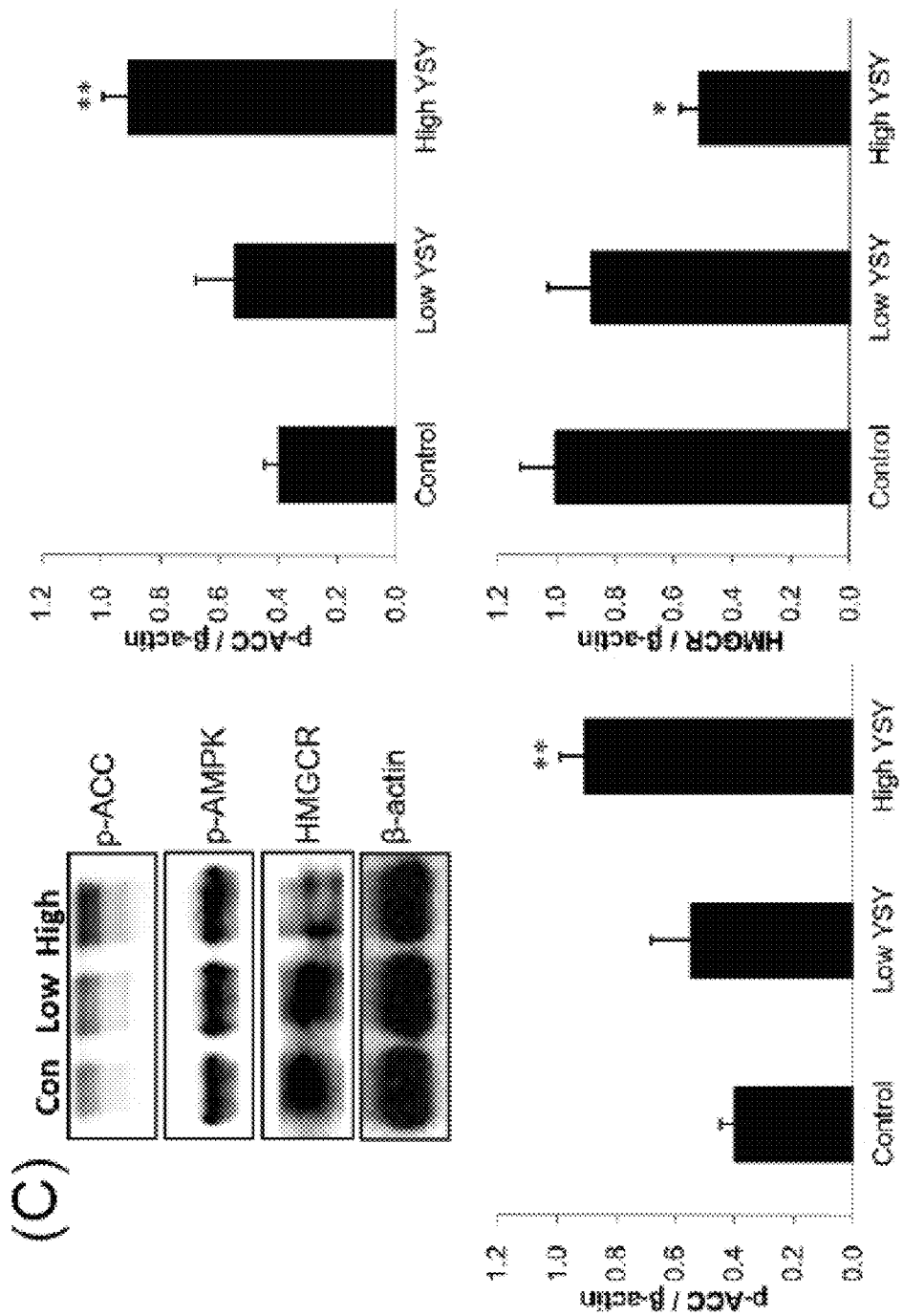

Example 3 YSY Ameliorates Hepatic Steatosis and Atherosclerosis in the HFD-Fed Mice The inhibitory effect of YSY on visceral WTA revealed its potential effect to prevent obesity. In this study, liver and aorta were harvested for histopathological assay, and our data demonstrated that high-dose YSY treatment can decrease hepatic steatosis and atherosclerosis (FIGS. 3A and 3B). Numerous researches indicated that AMPK pathway is one of the main regulators for lipid metabolism which influences progression of fatty liver and atherosclerosis (Beg, Allmann, & Gibson, 1973; Carlson & Kim, 1973). Our data also demonstrated that YSY promoted lipid metabolism through increasing phosphorylation levels of AMPK and ACC proteins as well as decreasing the expression level of HMGCR (FIG. 3C).

Example 4 YSY Improves Hyperlipidemia in the Human Subjects

The human subjects suffered from hyperlipidemia were recruited to confirm the hypolipidemic effects of YSY in animal model. The clinical results indicated that except in the normal group, YSY can significantly reduce serum levels of TC and TG in both borderline and high groups after 2 months of administration (Table 2).

| Retention Time | Peak Area | Percentage of weight | Relative Height |
|---|---|---|---|
| 0.565 | 698 | 0.10 | 0.0965 |
| 0.751 | 893 | 0.13 | 0.0470 |
| 1.175 | 70 | 0.01 | 0.0074 |
| 2.307 | 71966 | 10.11 | 23.4407 |
| 2.995 | 53663 | 7.54 | 2.4072 |
| 3.978 | 282367 | 39.67 | 12.5603 |
| 5.943 | 244255 | 34.31 | 6.7734 |
| 6.931 | 18882 | 2.65 | 0.5328 |
| 7.966 | 2449 | 0.34 | 0.1309 |
| 8.361 | 341 | 0.05 | 0.0037 |
| 9.224 | 29862 | 4.19 | 0.9513 |
| 10.879 | 4930 | 0.69 | 0.1585 |
| 11.709 | 1053 | 0.15 | 0.0570 |
| 12.303 | 139 | 0.02 | 0.0185 |
| 12.766 | 304 | 0.04 | 0.0130 |

TABLE 2

Serum biochemistry profile in the human subjects treated with YSY.

| | Normal group (n = 3) | | Borderline group (n = 3) | | High group (n=12) | |
|---|---|---|---|---|---|---|
| | Before | After | Before | After | Before | After |
| TC (mg/dL) | 161.5 ± 6.8 | 164.3 ± 11.4 | 229.3 ± 2.7 | 206.6 ± 10.1[a] | 254.4 ± 3.9 | 239.2 ± 5.3[a] |
| TG (mg/dL) | 87 ± 6 | 71 ± 11 | 181.7 ± 6.5 | 171 ± 10.6[a] | 278.2 ± 22.4 | 214.5 ± 27[a] |

Borderline group (TC: 200-239 mg/dL) and High group (TC: ≥240 mg/dL). Wilcoxon Signed Rank test was used to test for significant differences among three groups. The association between nutrition treatment and patient groups was evaluated with Chi square test.
[a]p < 0.05 compared to the basal level before the treatment at same group.

Figure 4:
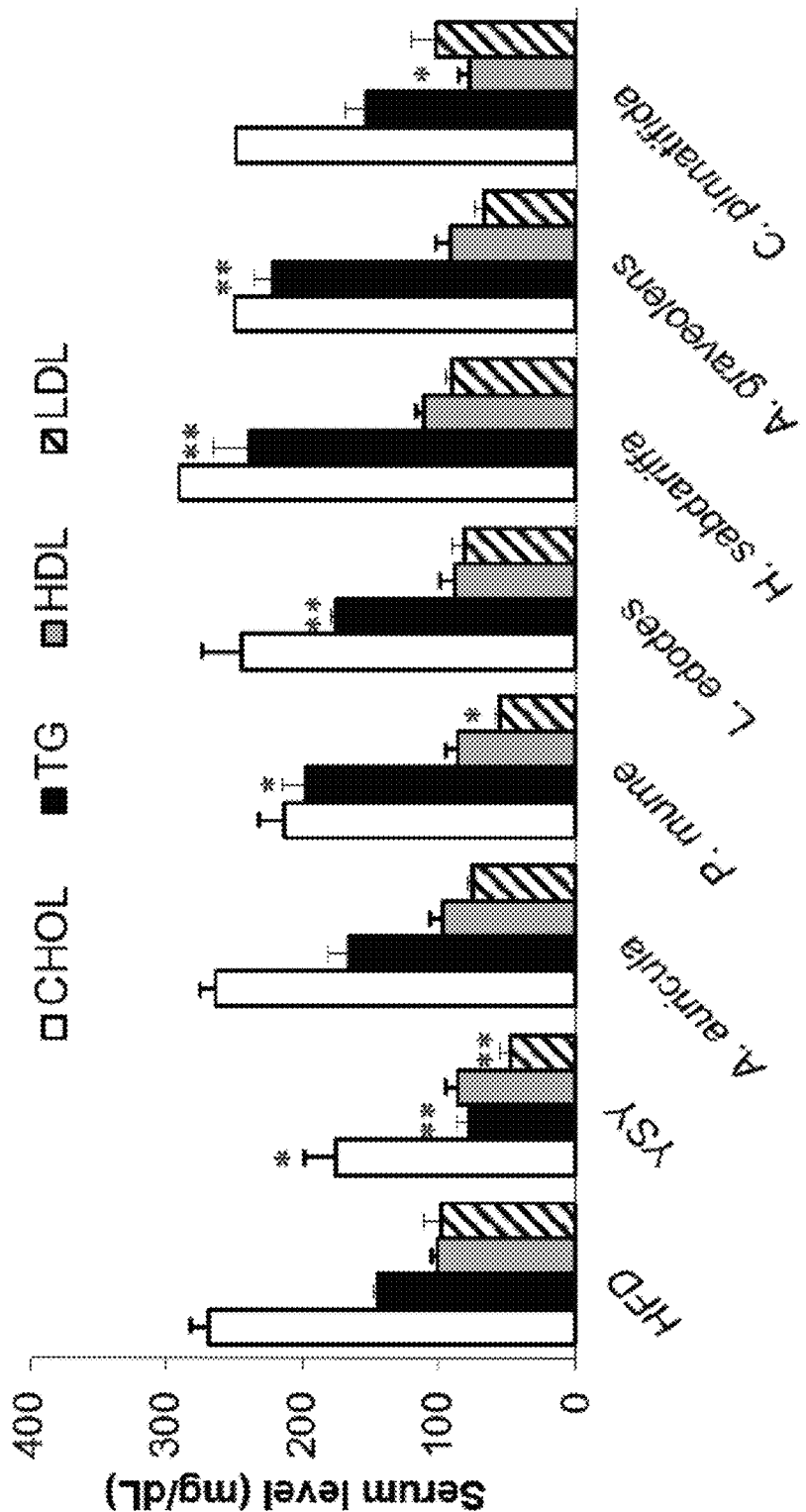
FIG. 4 shows comparison of anti-hyperlipidemic effect among YSY and its single plant ingredients in a hamster model of hyperlipidemia. * p<0.05 and ** p<0.01 compared to the group treated with high-fat diet (HFD) alone.

Example 5 YSY Exhibits the Best Anti-Hyperlipidemic Effect than Individual Plant Ingredients in the HFD-Fed Hamsters Experimental result indicated that only *P. mume* extract showed a reduction effect on the level of serum LDL at administration dose (1.48 g/kg/day; FIG. 4). Interestingly, YSY exhibited multiple and significant inhibitions on the serum levels of cholesterol, TG and LDL under the same dose.

Example 6 Chromatography Profile and Bioactive Compounds of YSY

Figure 5:
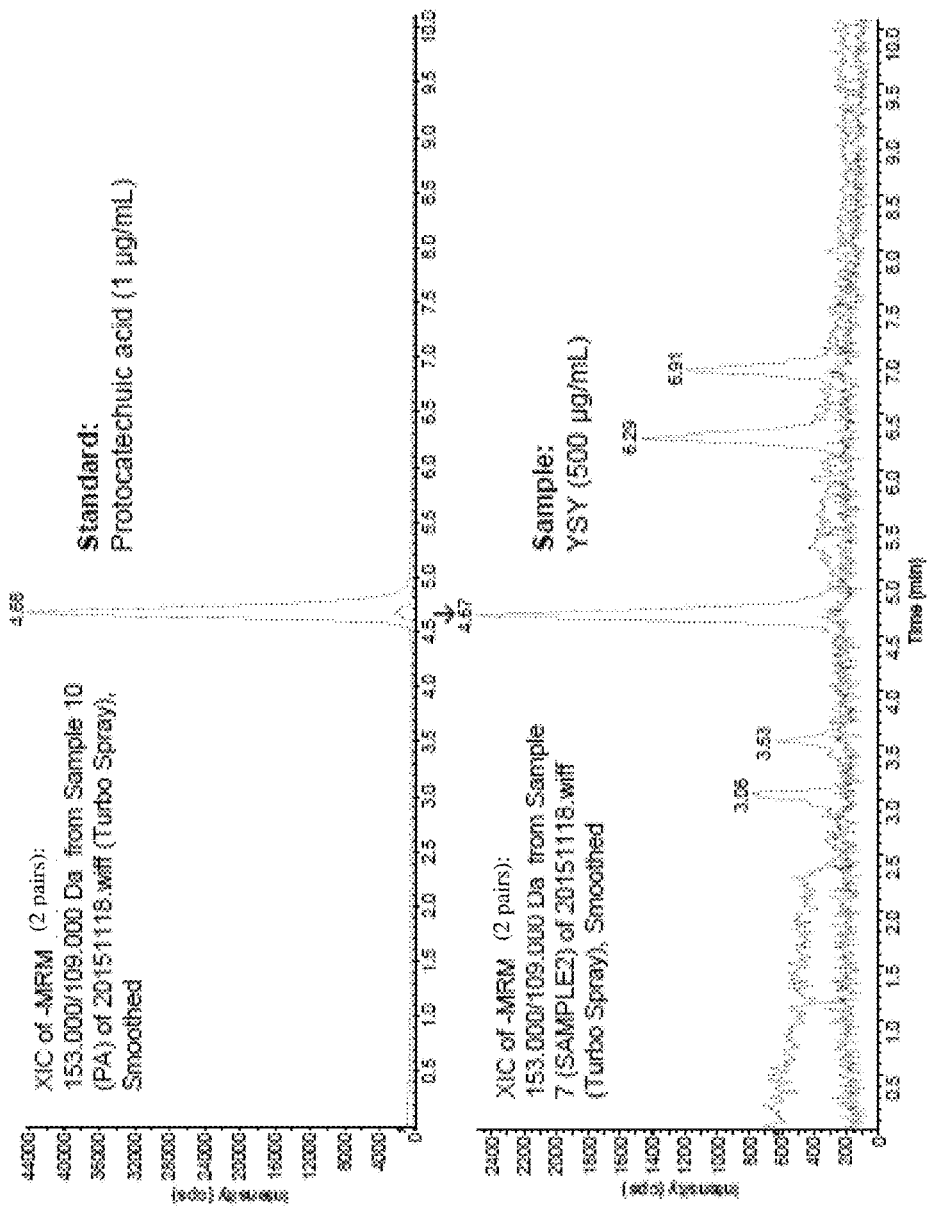
FIGS. 5 (A) and (B) show chromatography profile of YSY (Extracted ion chromatogram (XIC) of multiple reaction monitoring (MRM)). Two bioactive compounds, PCA (A) and CGA (B), were identified by HPLC-MS/MS analysis. The peaks corresponded to the reference compounds (PCA and CGA) within YSY were pointed out by the arrowhead on the chromatogram.
Figure 5:
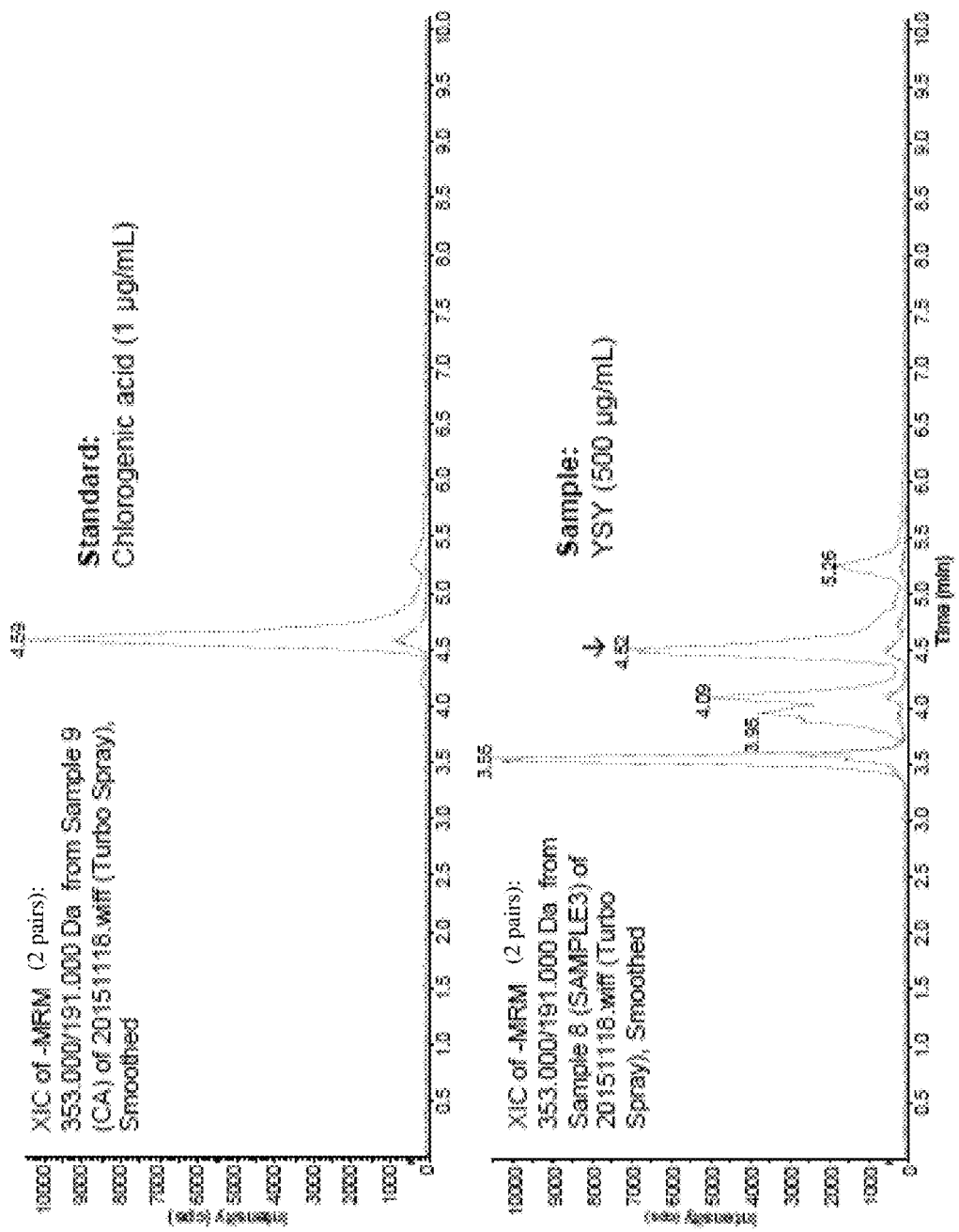

In our study, the standard compounds (PCA and CGA) were prepared as the concentration of 1 μg/mL. YSY (500 μg) were dissolved in 1 mL of water with subsequent filtration by 0.45 μm filter for HPLC. As shown in FIGS. 5A and 5B, MRM-based analysis mentioned that the retention time (RT) of PCA in YSY was 4.67 min as compared to the standard (RT=4.68 min), and the retention time of CGA in YSY was 4.52 min compared to the standard (RT=4.59 min).

Figure 6:
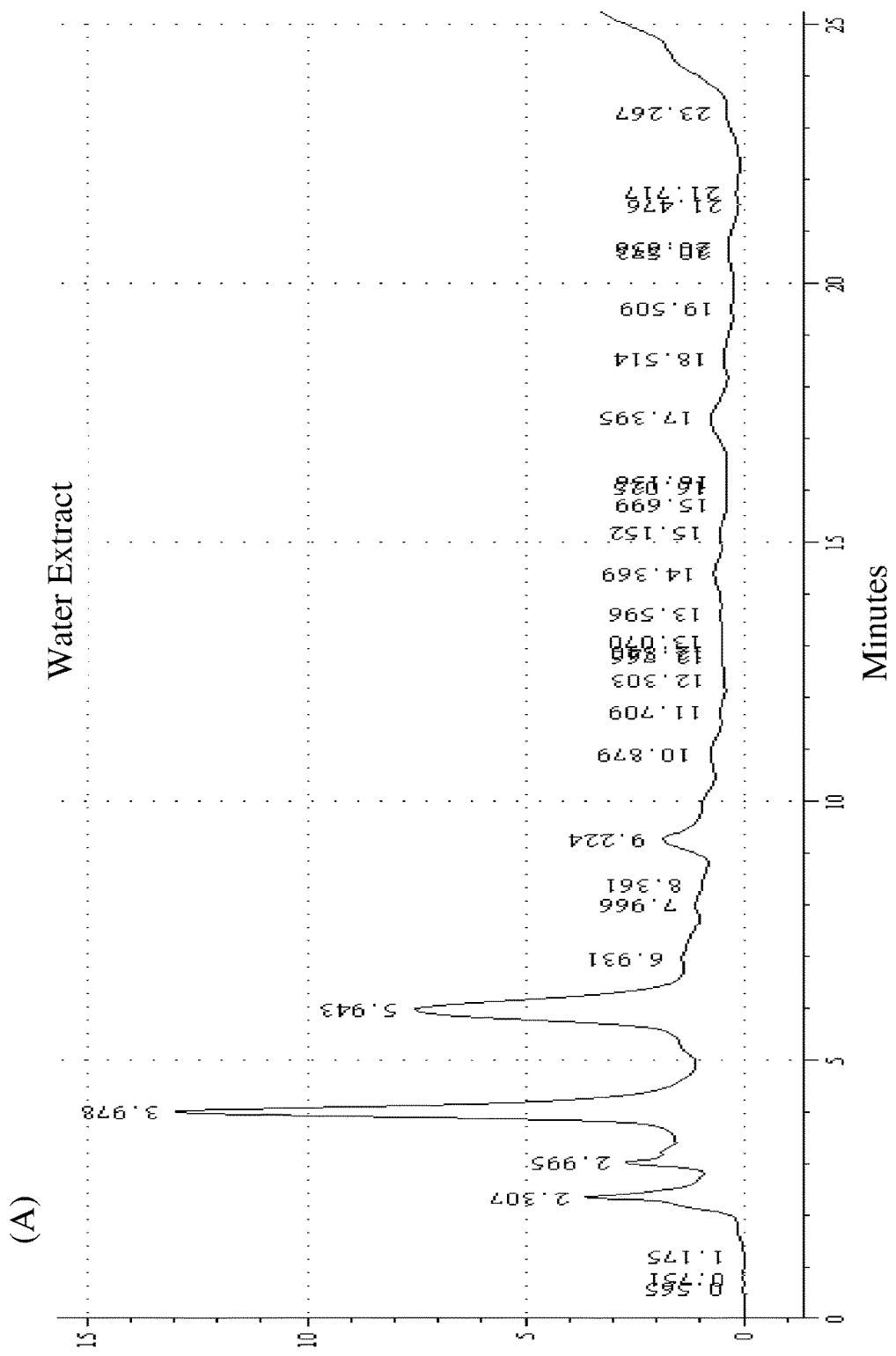
FIGS. 6 (A) and (B) show HPLC chromatography profile of YSY. The water extract (A) and alcohol extract (B) were identified by HPLC.
Figure 6:
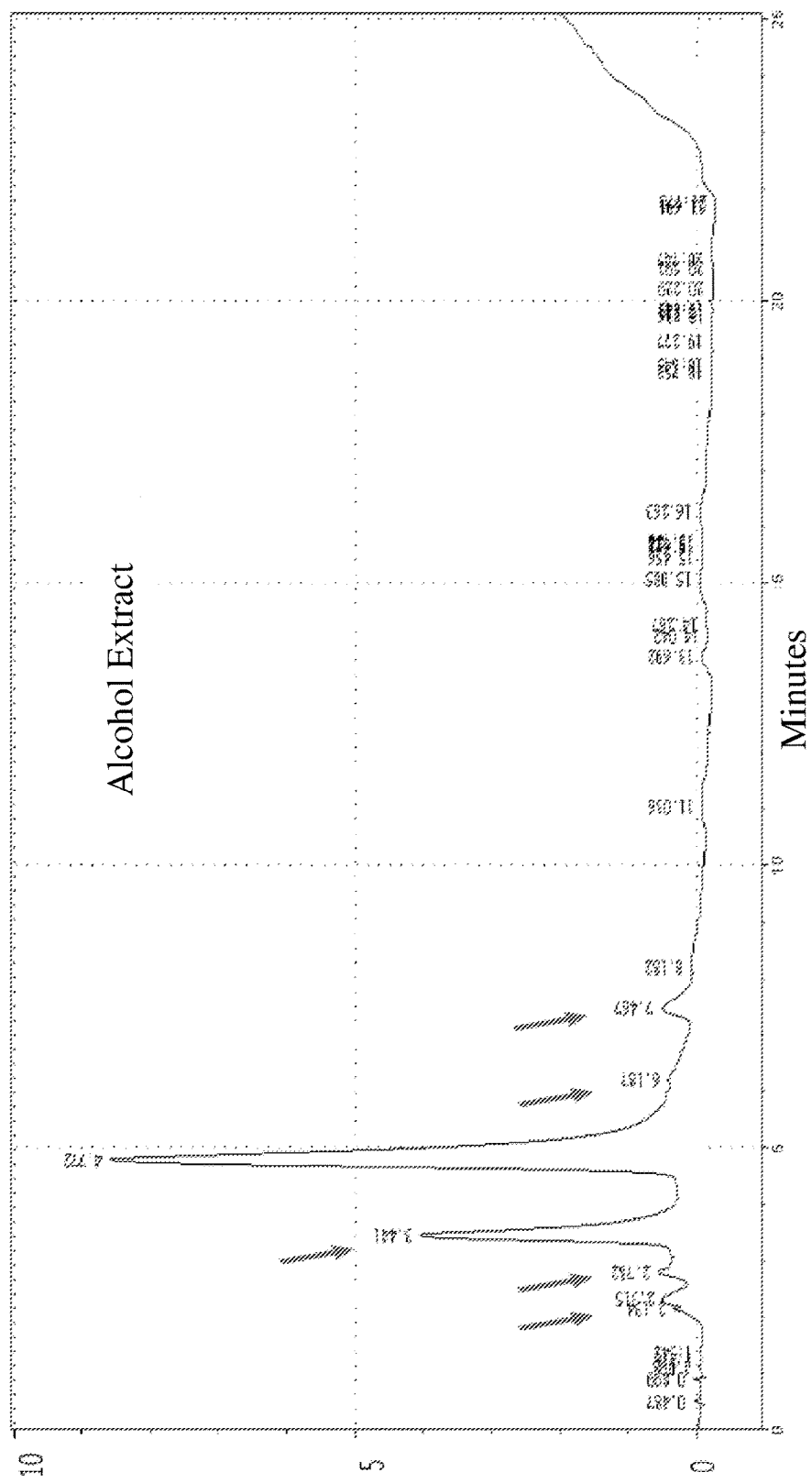

In addition, the water extract of YSY (FIG. 6A) and the alcohol extract of YSY (FIG. 6B) as comparison were analyzed by HPLC. The HPLC profiles are shown in FIG. 6 and the retention times, peak areas and relative heights of the peaks are shown in the table below.

What is claimed is:

1. A water extract of a composition comprising wood ear (*Auricularia auricular*), shiitake (*Lentinus edodes*), hawthorn fruit (*Crataegus pinnatifida*), roselle (*Hibiscus sabdariffa*), celery (*Apium graveolens*) and fruit of Chinese plum (*Prunus mume*), wherein the water extract is obtained by mixing wood ear, shiitake, hawthorn fruit, roselle, celery and fruit of Chinese plum to form a composition, soaking the composition in water for at least 16 hours at a temperature of about 50° C. to about 80° C. and boiling the resulting composition to obtain the water extract of the composition; wherein the wood ear, shiitake, hawthorn fruit, roselle, celery and fruit of Chinese plum in the composition are in a ratio of about 0.5 to about 1.5:about 0.5 to about 1.5:about 1.5 to about 2.5:about 1.5 to about 2.5:about 4.5 to about 5.5:about 0.5 to about 1.5, respectively, by dry weight; and wherein the composition comprises compounds having retention times at about 3.2 to about 4.5 minutes and about 5.4 to about 6.2 minutes, respectively, as measured by HPLC;

wherein the composition comprises compounds having retention times at about 4.61 minutes to 4.95 minutes, about 6.1 minutes to about 6.5 minutes, about 6.8 minutes to about 7.0 minutes, about 3.45 minutes to about 3.62 minutes and about 2.96 minutes to 3.16 minutes, respectively as measured by Extracted ion chromatogram (XIC) of multiple reaction monitoring (MRM), wherein the XIC of −MRM is detected at 153.000/109.000 Da of HPLC-MS/MS and protocatechuic acid is used as standard; or wherein the composition comprises compounds having retention times at about 4.35 minutes to about 4.65 minutes, about 3.41 minutes to about 3.62 minutes, about 4.0 minutes to about 4.15 minutes, about 3.8 minutes to about 4.0 minutes and about 5.18 minutes to about 5.4 minutes, respectively as measured by Extracted ion chromatogram (XIC) of multiple reaction (MRM), wherein the XIC of −MRM is detected at 153.000/109.000 Da of HPLC-MS/MS and chlorogenic acid is used as standard.

2. The water extract of claim 1, wherein the soaking the composition in water is for about 18 hours to about 48 hours.

3. The water extract of claim 1, wherein the soaking the composition in water is for about 24 hours.

4. The water extract of claim 1, wherein the soaking temperature is about 50° C. to about 75° C.

5. The water extract of claim 1, wherein the soaking temperature is about 60° C.

6. The water extract of claim 1, wherein the wood ear, shiitake, hawthorn fruit, roselle, celery and fruit of Chinese plum in the composition are in a ratio of about 1:about 1:about 2:about 2:about 5:about 1 by dry weight.

7. The water extract of claim 1, wherein the water extract further comprises a compound having a retention time at about 2.7 minutes to 3.2 minutes as measured by HPLC.

8. The water extract of claim 1, wherein the water extract further comprises one or more compounds having a retention time selected from the group consisting of about 2.7 minutes to 3.2 minutes, about 2.0 minutes to about 2.5 minutes, about 9.0 minutes to about 9.4 minutes and about 6.8 minutes to 7.1 minutes, as measured by HPLC.

9. The water extract of claim 1, which has an HPLC profile comprising fifteen peaks at the following retention times: 0.565, 0.751, 1.175, 2.307, 2.995, 3.978, 5.943, 6.931, 7.966, 8.361, 9.224, 10.879, 11.709, 12.303 and 12.766; wherein the peaks have peak area of 698, 893, 70, 71966, 53663, 282367, 244255, 18882, 2449, 341, 29862, 4930, 1053, 139 and 304, respectively; wherein the peaks have percentage of weight of 0.10, 0.13, 0.01, 10.11, 7.54, 39.67, 34.31, 2.65, 0.34, 0.05, 4.19, 0.69, 0.15, 0.02 and 0.04, respectively; and wherein the peaks have relative height of 0.0965, 0.0470, 0.0074, 23.4407, 2.4072, 12.5603, 6.7734, 0.5328, 0.1309, 0.0037, 0.9513, 0.1585, 0.0570, 0.0185 and 0.0130, respectively.

* * * * *